(12) United States Patent
Meyer et al.

(10) Patent No.: US 7,488,446 B2
(45) Date of Patent: *Feb. 10, 2009

(54) STERILIZED CONNECTOR APPARATUS AND METHOD OF COUPLING A BIOPROCESSOR TO A MEDIA SOURCE

(75) Inventors: David W. Meyer, Jordan, MN (US); Joseph M. Whall, River Falls, MN (US)

(73) Assignee: Colder Products Company, St. Paul, MN (US)

( * ) Notice: Subject to any disclaimer, the term of this patent is extended or adjusted under 35 U.S.C. 154(b) by 441 days.

This patent is subject to a terminal disclaimer.

(21) Appl. No.: 10/960,267

(22) Filed: Oct. 7, 2004

(65) Prior Publication Data

US 2005/0084410 A1   Apr. 21, 2005

Related U.S. Application Data

(62) Division of application No. 10/097,073, filed on Mar. 12, 2002, now Pat. No. 6,871,669.

(60) Provisional application No. 60/276,612, filed on Mar. 16, 2001.

(51) Int. Cl.
*A61L 2/00* (2006.01)
*F16K 11/00* (2006.01)

(52) U.S. Cl. ............................... 422/1; 137/862

(58) Field of Classification Search ................ 137/862, 137/605, 614; 252/344, 349; 422/1, 7, 22
See application file for complete search history.

(56) References Cited

U.S. PATENT DOCUMENTS

| 2,631,001 | A | | 3/1953 | Griswold |
| 3,094,306 | A | | 6/1963 | Conrad |
| 3,151,640 | A | | 10/1964 | Teston |
| 3,918,484 | A | | 11/1975 | Lamb |
| 4,742,851 | A | | 5/1988 | Lundblade |
| 5,494,074 | A | * | 2/1996 | Ramacier et al. ....... 137/614.04 |
| 5,555,908 | A | | 9/1996 | Edwards et al. |
| 6,085,602 | A | * | 7/2000 | Schorn et al. ............ 73/863.83 |
| 6,140,657 | A | * | 10/2000 | Wakalopulos et al. .... 250/492.3 |

FOREIGN PATENT DOCUMENTS

| DE | 736348 | 6/1973 |
| DE | 44 14 275 | 10/1995 |
| FR | 1.397.760 | 4/1965 |
| FR | 1.488.386 | 7/1967 |
| JP | 02195866 | 8/1990 |
| JP | 05049683 | 8/1991 |

* cited by examiner

*Primary Examiner*—Elizabeth L McKane
*Assistant Examiner*—Kevin C Joyner
(74) *Attorney, Agent, or Firm*—Merchant & Gould P.C.

(57) ABSTRACT

A disposable connector apparatus designed for one time use in a bioprocessing assembly, and a method for coupling a piece of bioprocessing equipment to a media source in a sterilized environment. The connector apparatus includes a telescoping valve formation with an actuation incorporating a one way lock mechanism that cannot be disconnected.

6 Claims, 7 Drawing Sheets

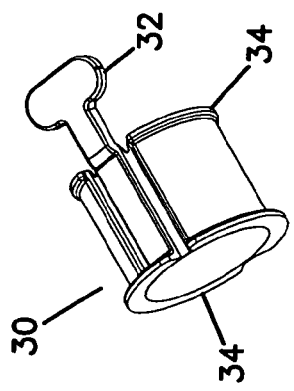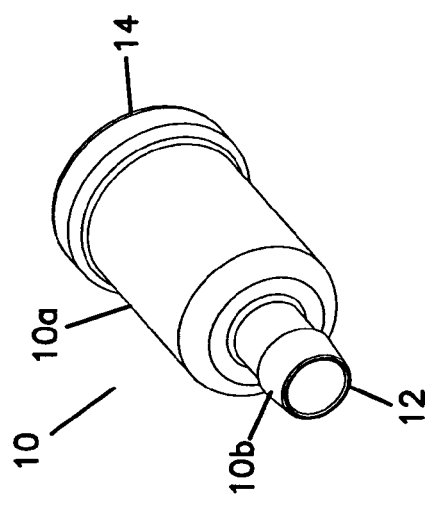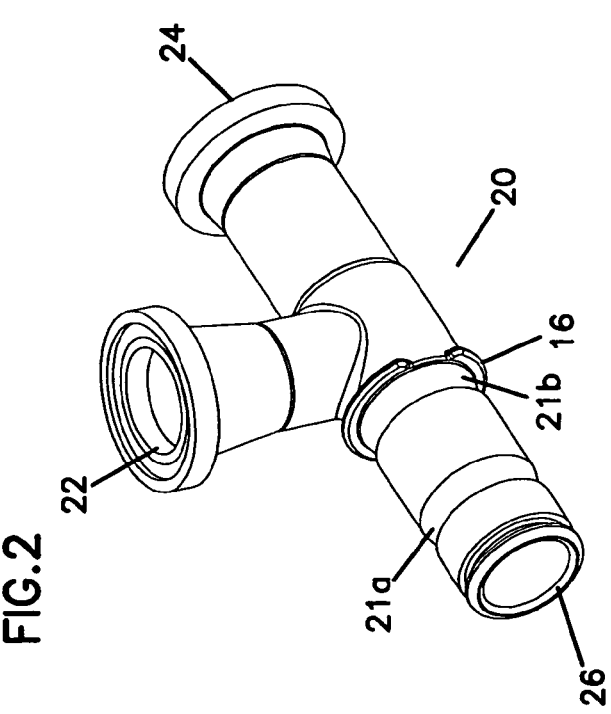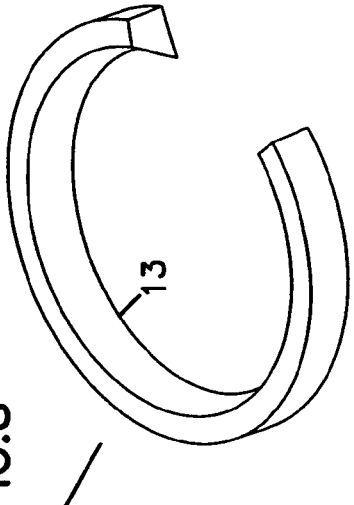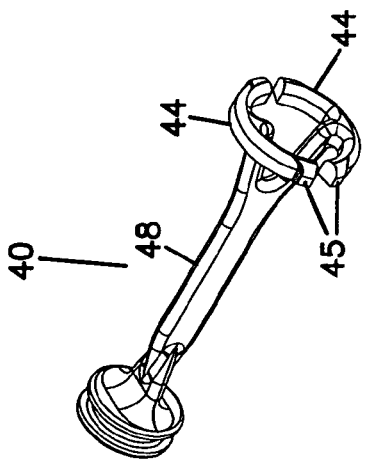

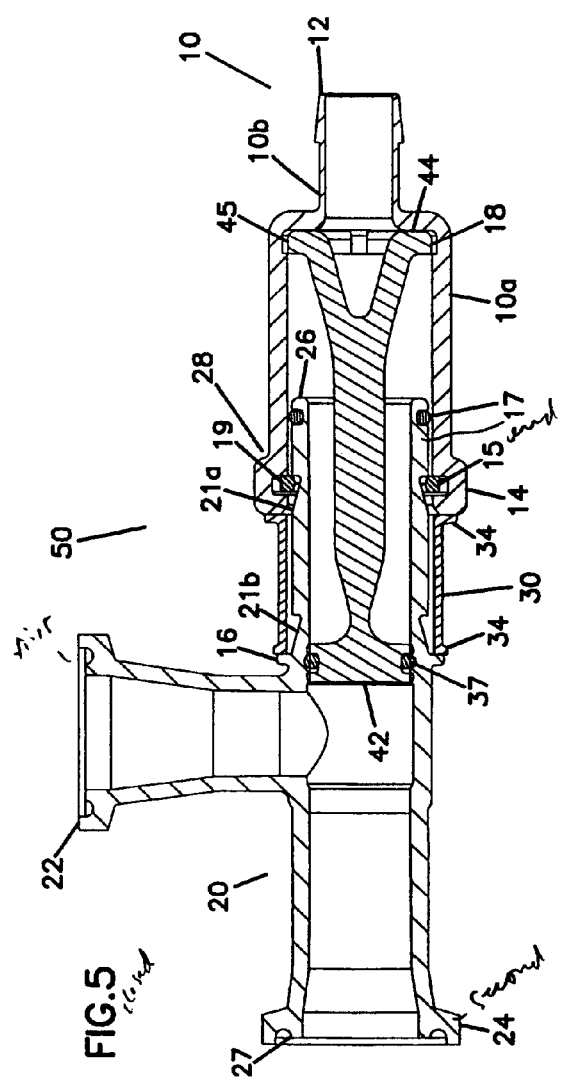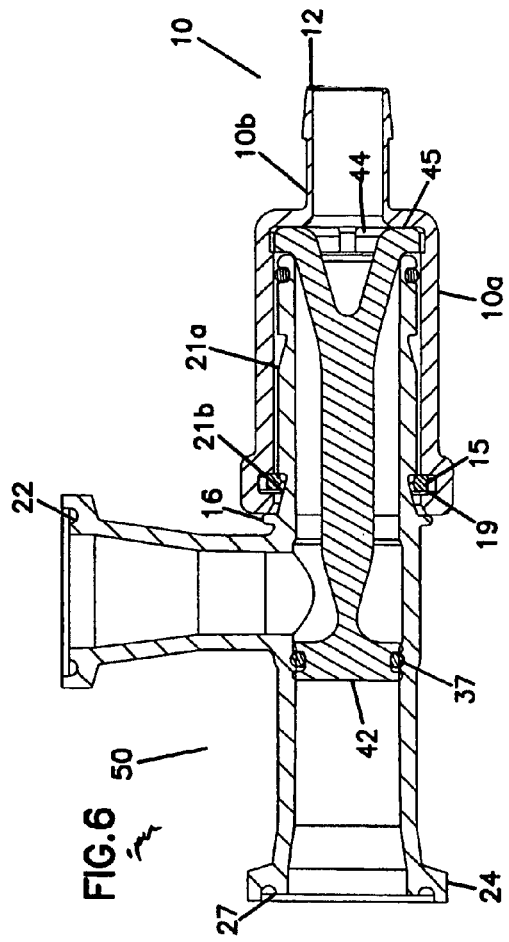

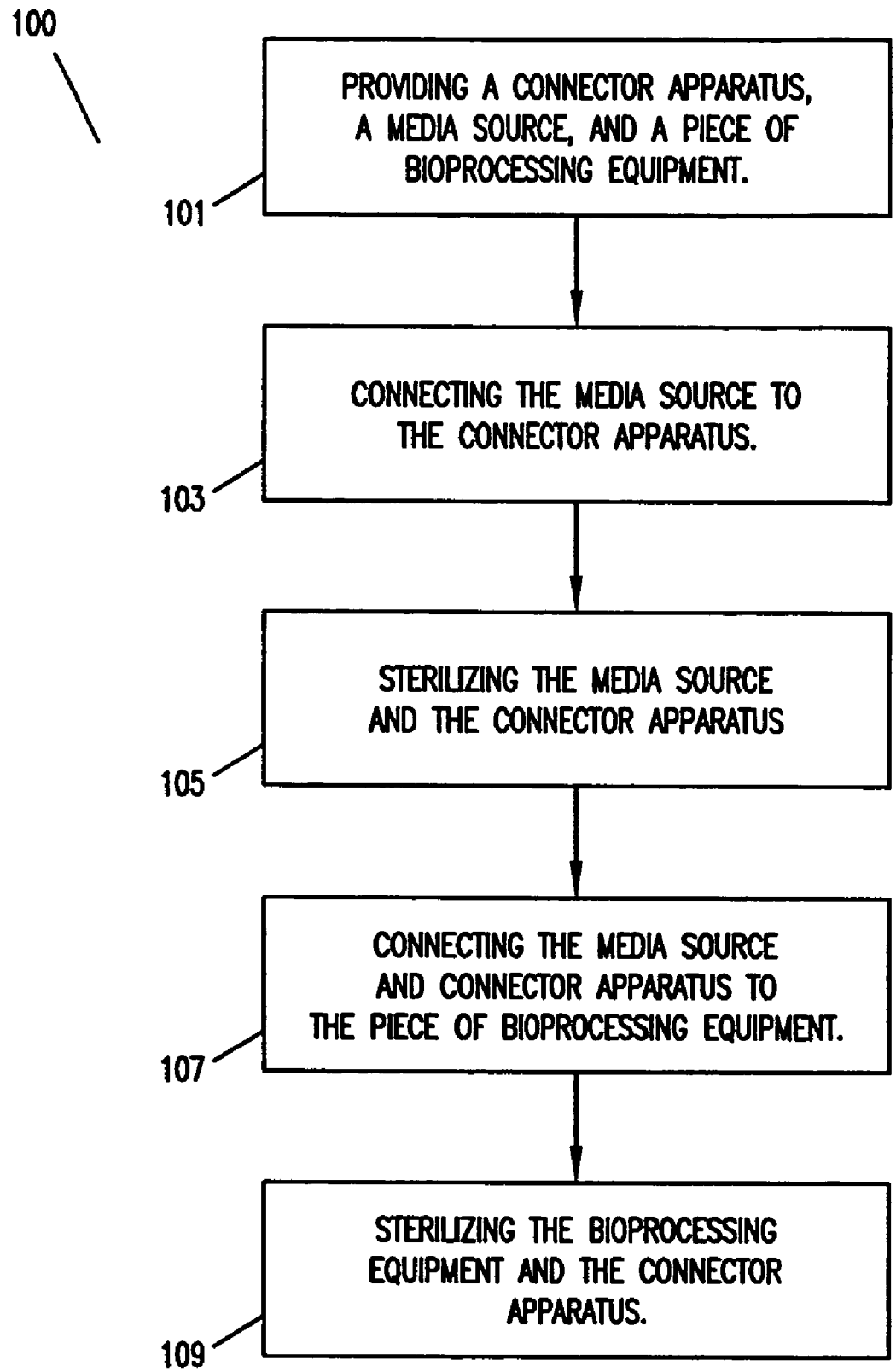

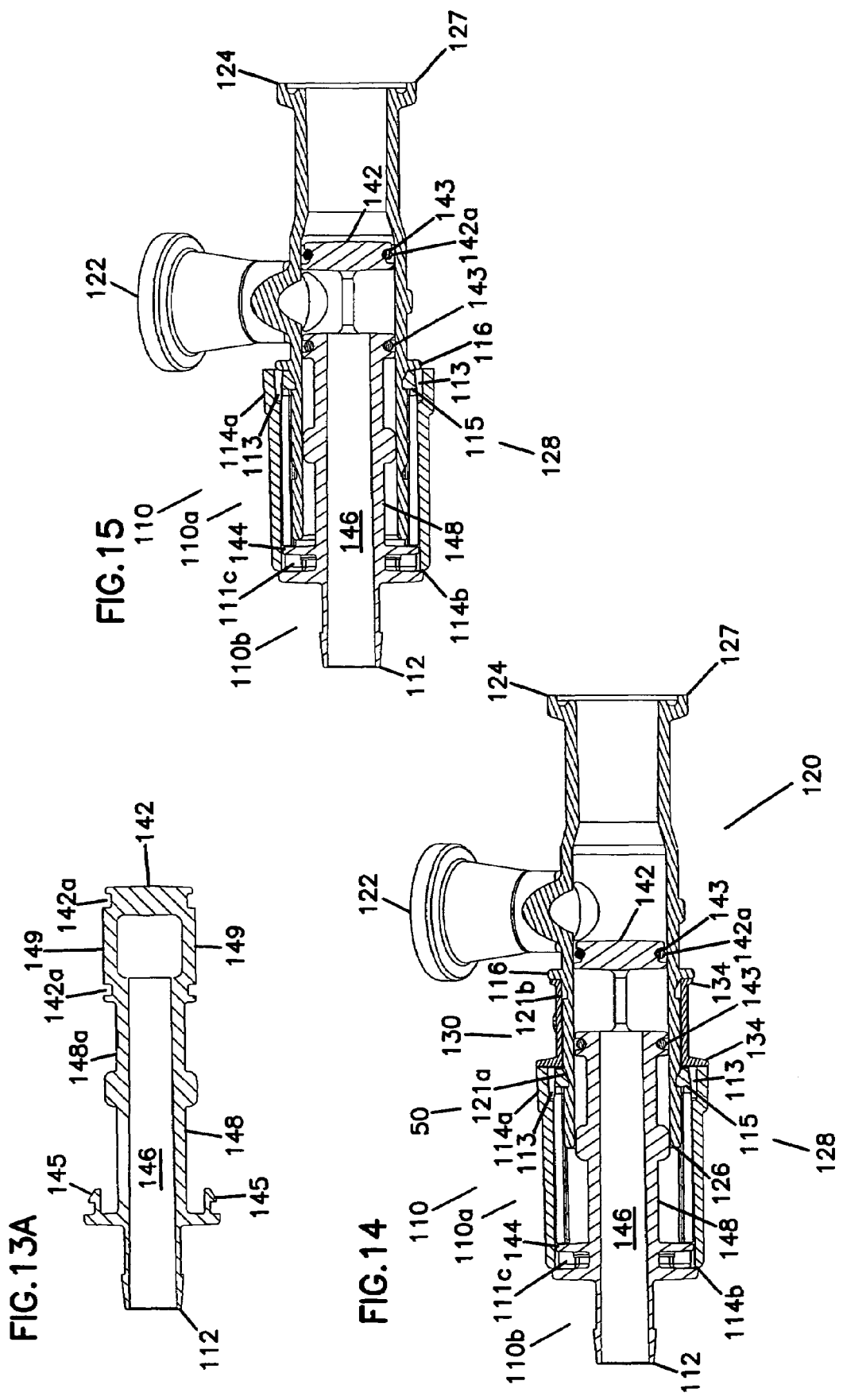

US 7,488,446 B2

STERILIZED CONNECTOR APPARATUS AND METHOD OF COUPLING A BIOPROCESSOR TO A MEDIA SOURCE

RELATED APPLICATION

This application is a Divisional of application Ser. No. 10/097,073, now U.S. Pat. No. 6,871,669 filed Mar. 12, 2002 which is a non-provisional application Ser. No. 60/276,612, filed Mar. 16, 2001. This application claims the benefit of Provisional Application, U.S. Ser. No. 60/276,612, filed on Mar. 16, 2001, entitled Sterilized Connector Apparatus and Method of Coupling a Bioprocessor to a Media Source, which is incorporated herewith by reference.

FIELD OF THE INVENTION

This invention relates to an apparatus for a connector apparatus and a method for implementing the same. More particularly this invention relates to a connector apparatus for coupling a media source to a bioreactor in a sterilized environment.

BACKGROUND OF THE INVENTION

Bioprocessing systems, used for instance, in culturing biomaterial or producing and designing drugs used in pharmaceutical applications is a widely common technique. Typically, these systems employ bioreactors and media dispensers connected by tube and valve assemblies. Multiple steam traps and a flow hood are often incorporated to sterilize the system from contaminants. Typically, bioreactors or culture environments and media dispensers have consisted of large vats for producing such biomaterials. Typically, the components used in the assembly were reusable stainless steel components. However, this would require a complex and time consuming coupling procedure. In addition, flow hoods, such as laminar flow hoods, seem to be very cumbersome and inconvenient as they are moved in and out of the processing environment. As more specific cultures and designer drugs are being produced, and as more specific growth media provided to a bioreactor are being developed, there is a need for an improved and less complex bioprocessing system.

Furthermore, present designs using multiple steam traps and complex tube/valve assemblies create a bioprocessing system that is difficult to operate and may allow for increased margin of error with respect to sterilization of the system. Therefore, there is a need for a less complex system that is more convenient to handle, and that can simplify the more specific pharmaceutical designs associated with particular biomaterial production.

The present invention, as described hereinbelow, provides improvements upon one or more of the above described and other shortcomings of existing bioprocessing systems and their valve assemblies.

SUMMARY OF THE INVENTION

In accordance with the present invention, the above and other problems were solved by providing a connector apparatus and a sterilized assembly for bioprocessing using the connector apparatus. In addition, a method for implementing a connector apparatus is provided.

In one embodiment of the present invention, a connector apparatus includes a coupler and a connector valve having a valve member all of which are disposable after one time use.

In one embodiment, the coupler has an end that attaches to a connector valve, and an outlet for attachment to a piece of bioprocessing equipment. The connector valve includes a connecting mechanism for connecting to the coupler, and an end for attachment to a media source. The connector valve and the coupler can be connected telescopically. The connector valve includes a valve member connected thereto and is moveable with respect to the coupler to actuate the connector apparatus from a closed position to an open position. The coupler further contains retaining recesses, and the connector valve includes a locking member. The locking member cooperates with the above retaining recesses in engaging the connector valve to the coupler in both the closed and the open configurations. The retaining recesses are tapered such that they do not allow for the connector valve and the coupler to be detached once connected, whereby the connector valve is permanently engaged with the coupler once connected, and the connector apparatus may be designed to be disposable after one time use.

In another embodiment of the present invention, an assembly for bioprocessing includes a piece of bioprocessing equipment, a media source connected to a connector apparatus both of which are disposable after one time use. The piece of bioprocessing equipment may be connected to a steam source for sterilization of the piece of bioprocessing equipment in a culture environment. The connector apparatus is as described in the above embodiment. Further, the connector apparatus includes a removable stop member, which prevents movement of the connector valve into the open configuration, such that no fluid flow is allowed from the media source through the connector apparatus. The stop member may be removed when the assembly is to be actuated, allowing the connector apparatus to be actuated from the closed configuration to the open configuration allowing flow from the media source to the piece of bioprocessing equipment.

In one embodiment, the media source may be connected to the connector apparatus both prior to assembly use, and during assembly use, where a first portion of the connector apparatus, including the media source are gamma sterilized at a media filling station. Furthermore, a second portion of the connector apparatus may be steam sterilized in a bioprocessing environment where the connector apparatus and media source may be connected to the piece of bioprocessing equipment.

In a further embodiment, a method for connecting a media source to a piece of bioprocessing equipment includes providing a connector apparatus connected to a media source. The connector apparatus, as described above, includes a coupler and a connector valve having a valve member, wherein the connector apparatus can couple the piece of bioprocessing equipment to the media source for receiving materials from the media source. A first portion of the connector apparatus may be gamma sterilized with the media source at a media filling station, and a second portion of the connector apparatus may be steam sterilized in a bioprocessing environment where the connector apparatus is to be connected. A stop member, attached onto the coupler, prevents movement of the connector valve from a closed configuration to an open configuration, and is removed so that the coupler and the connector valve can be actuated to the open configuration. The coupler apparatus along with the media source can be disposable after one time use.

An advantage of the present invention is that the employment of a connector apparatus can greatly simplify the parts of a coupling mechanism in a bioprocessing system. Further, it can eliminate the need for cumbersome laminar flow hoods and complex valve assemblies that may use multiple steam traps. As the present invention is intended for one time use only, it can be discarded after use providing further convenience over other systems.

These and other various advantages and features of novelty, which characterize the invention are pointed out in the following detailed description. For better understanding of the invention, its advantages, and the objects obtained by its use, reference should also be made to the drawings which form a further part hereof, and to accompanying descriptive matter, in which there are illustrated and described specific examples of an apparatus in accordance with the invention.

BRIEF DESCRIPTION OF THE DRAWINGS

Referring now to the drawings in which like reference numbers represent corresponding parts throughout:

FIG. 2 represents a perspective view of an embodiment of a coupler in a connector apparatus as in FIG. 1, in accordance with the principles of the present invention.

FIG. 3 represents a perspective view of an embodiment of a connector valve in a connector apparatus as in FIG. 1, in accordance with the principles of the present invention.

FIG. 4 represents a perspective view of an embodiment of a stopping member for a connector apparatus as in FIG. 1, in accordance with the principles of the present invention.

FIG. 5 represents a side cross-sectional view of an embodiment of the connector apparatus of FIG. 1 including an embodiment for a valve member positioned in an embodiment for a closed configuration in accordance with the principles of the present invention.

FIG. 6 represents a side cross-sectional view of an embodiment of the connector apparatus of FIG. 1 including an embodiment for a valve member positioned in an embodiment for an open configuration in accordance with the principles of the present invention.

FIG. 7 represents a side view of the valve member shown in FIGS. 5 and 6.

FIG. 8 represents perspective view of one embodiment for a retaining ring, also shown in FIGS. 5 and 6, engaged in a first position (FIG. 5) and a second position (FIG. 6), in accordance with the principles of the present invention.

FIG. 9 represents a flow diagram of an embodiment for a method of coupling a media source to a piece of bioprocessing equipment in accordance with the principles of the present invention.

FIG. 13a represents a sectional view of the valve member of FIG. 13.

FIG. 14 represents a sectional view of an embodiment of the connector apparatus of FIG. 1 including an embodiment for a valve member positioned in an embodiment for a closed configuration in accordance with the principles of the present invention.

FIG. 15 represents a sectional view of an embodiment of the connector apparatus of FIG. 1 including an embodiment for a valve member positioned in an embodiment for an open configuration in accordance with the principles of the present invention.

DETAILED DESCRIPTION OF THE PREFERRED EMBODIMENT

In the following description of the illustrated embodiments, reference is made to the accompanying drawings that form a part hereof, and in which is shown by way of illustration of the embodiments in which the invention may be practiced. It is to be understood that other embodiments may be utilized as structural changes may be made without departing from the spirit and scope of the present invention.

The present invention provides a connector apparatus for coupling a media source to a piece of bioprocessing equipment.

Figure 1:
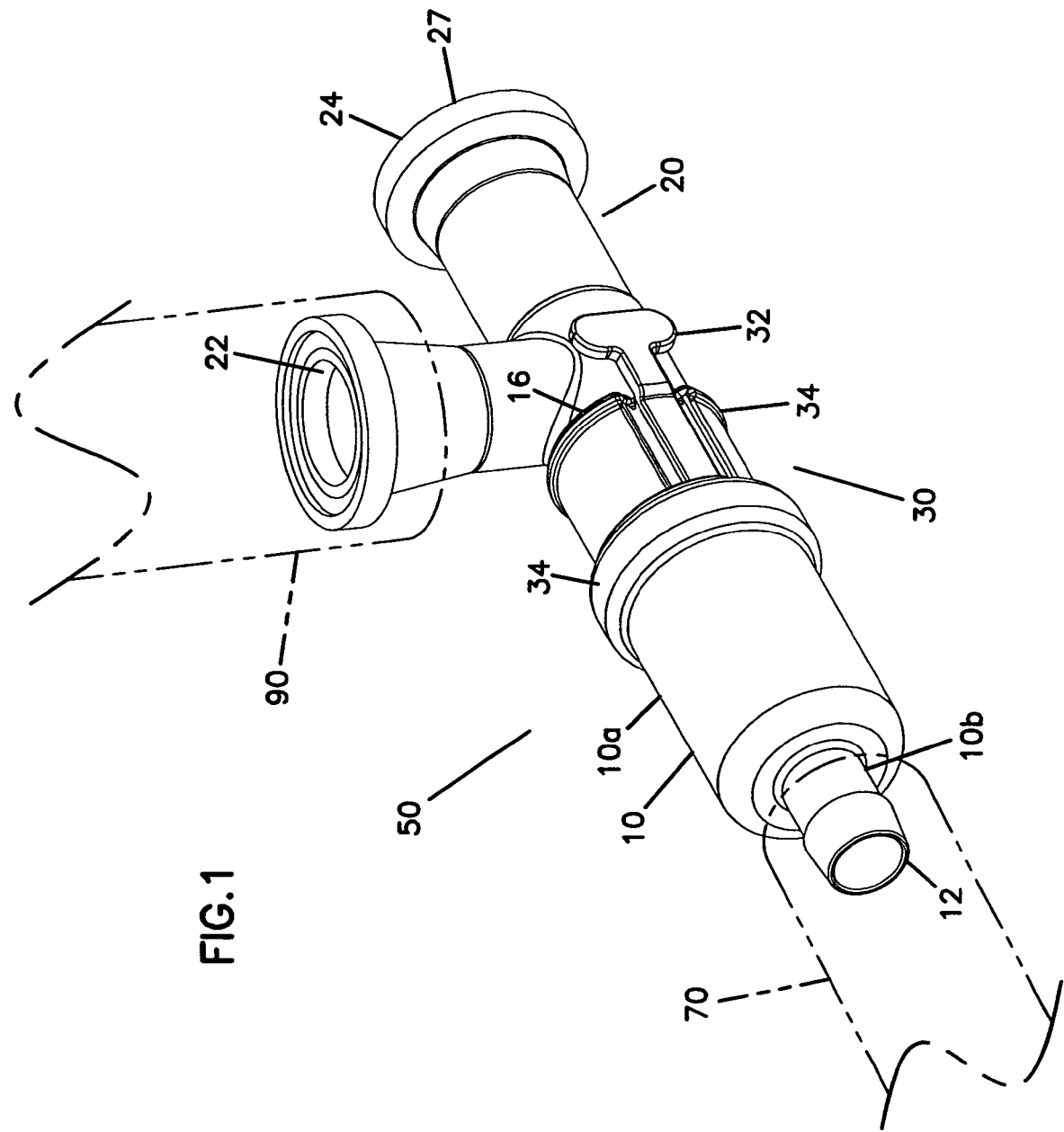
FIG. 1 represents a side view of one embodiment for a connector apparatus in accordance with the principles of the present invention.

FIG. 1 illustrates a connector apparatus 50 connecting a media source 70 to a piece of bioprocessing equipment 90.

In FIG. 1, the connector apparatus 50 includes a coupler 20 and a connector valve 10 that includes a valve member 40 connected thereto (shown in FIGS. 5-7). As shown in FIG. 1, the connector valve 10 contains an end 12 suitable for attachment to the media source 70 and a connecting mechanism 28 (best shown in FIG. 5) for connection to the coupler 20. The connector valve 10 includes an adapter 10a and the end 12 may define a hose portion 10b. As shown in FIG. 5, the connecting mechanism 28 includes a locking member 15 partially residing in a groove 19. The connecting mechanism 28 may be connected to or disposed at the head 14 of the adapter 10a. The function of the connecting mechanism 28 will be further detailed below. The end 12, as depicted in FIG. 1, is shown as a barbed end for attachment to a media source, such as 70. However, there may be other interfaces that can be used to achieve the same result.

The coupler 20 has an outlet 22 for passage of media and connection to the piece of bioprocessing equipment 90, such as but not limited to a bioreactor. The outlet 22, as depicted in FIG. 1, is shown as a sanitary flange. However, there may be other interfaces that can be used to achieve the same result. Also depicted is a second outlet 24 for allowing steam passage to a steam trap or a condensate outlet. A similar sanitary flange 27 as in the outlet 22 may be disposed at the second outlet 24. However, it will be appreciated that an O-ring seal also can be used at the second outlet 24. In one embodiment, the connector valve 10 and the coupler 20 are telescopically connected, wherein the head 14 may be the receiving female member and an end 26 (shown in FIG. 2) may be the inserting male member. The end 26 (inserting male member) can further have an O-ring seal 17 (shown in FIGS. 5 and 6) for providing a fluid tight seal.

The coupler 20 may be insertable through a stop member 30, such that the stop member 30 may be releasably attached around the coupler 20. Stop tabs 34 of the stop member 30 prevent further movement of the connector valve 10 towards the first and second outlets 22 and 24, respectively. One of the stop tabs 34 of the stop member 30 abuts the head 14 of the connector valve 10 to restrict telescopic movement between the connector valve 10 and the coupler 20. Another stop tab 34 abuts a seating portion 16 to further restrict movement of the stop member 30 and connector valve 10. Further, the stop member 30 maintains the apparatus 50 in a closed configuration. The stop member 30 further includes a disconnect handle 32, such that removal of the handle allows removal of the entire stop member 30, and the connector apparatus 50 may be actuated to an open configuration. The handle 32 may be a tear away handle such that tearing the handle 32 enables the entire stop member 30 to be removed. FIGS. 2-4 depict individual views of the coupler 20, connector valve 10, and the stop member 30.

FIGS. 5 and 6 illustrate an embodiment for the connector apparatus 50 in an initial closed configuration and an embodiment of an open configuration. In FIG. 5, the coupler 20 is provided with first and second tapered retaining recesses 21A and 21B, respectively, wherein the connector valve 10 is initially disposed at the first retaining recess 21A. The first and second tapered recesses 21A, 21B respectively define two locations for the connecting mechanism 28 of the connector valve 10 to engage the coupler 20. The two locations include a first location that defines the closed configuration of the connector apparatus 50 and a second location that defines the open configuration of the connector apparatus 50. The connector valve 10 further contains the connecting mechanism 28 that includes a locking member 15, illustrated as a retaining ring, localized in a first groove 19 disposed about the inner surface of the head 14 of the adapter 10a. The locking member 15 is positioned such that portion of the locking member 15 is insertable into the first groove 19 of the adapter 10a and a remaining portion containing a tapered side 13 of the locking member 15 (also shown in FIG. 8) protrudes radially outside from the first groove 19. The locking member 15 of the connecting mechanism engages the first recess 21A of the coupler 20 in the closed configuration, connecting the connector valve 10 to the coupler 20. The first tapered recess 21A and the tapered side 13 have a connection wherein the first tapered recess 21A has a transverse edge with respect to a tapered portion of the recess 21A. The first tapered recess 21A locks the locking member 15 from moving in a backward direction and prevents the connector valve 10 from disconnecting from the coupler 20 once they are connected. The tapered portion of the first recess 21A and the tapered side 13 of the locking member 15 allow only for forward movement towards the second tapered recess 21B.

As illustrated in FIG. 7, one embodiment of a valve member 40 is provided with an elongated structural frame 48, and a retaining end 44 that includes extension tabs 45. The frame 48 is structured and configured so as to enable fluid flow through the connector valve 10 from the end 12 to the head 14. A retaining structure illustrated as second groove 18 disposed at the end 12 provides insertion for the extension tabs 45, thereby connecting the valve member 40 to the adapter 10a such that the valve member 40 is moved when the connector valve 10 is moved. Preferably, the valve member 40 is partially disposed within the adapter 10a. The valve member 40 also has a sealing end 42. The sealing end 42 may be insertable into the coupler 20, and may include an O-ring seal 37. When a media source, such as media source 70, and the connector valve 10 are sterilized in a first sterilization step (further discussed below), the sealing end 42 can provide a sterile barrier between a sterilized portion including the connector valve 10 through a portion of the coupler 20. The O-ring seal 37 provides a suitable seal between the sealing end 42 and a sidewall of the coupler 20, whereby the first sterilization step would sterilize at least the connector valve 10 including the end 12, head 14, and through to the O-ring seal 37 of the sealing end 42. In the closed configuration, the sealing end 42 of valve member 40 forms a fluid tight seal upstream of the outlet 22 preventing flow of media through the connector apparatus 50. In the open configuration, the sealing end 42 of the valve member 40 forms a fluid tight seal downstream of the outlet 22 sealing the second outlet 24.

The stop member 30 may be attached around the coupler 20. Stop tabs 34 may be disposed on ends of the stop member 30 such that they abut the head 14 of the connector valve 10, and abut a seating portion 16 of the coupler 20. The seating portion 16 may be disposed circumferentially about the coupler 20 and before the outlet 22 of the coupler 20 (see FIG. 1). Stop tabs 34 of the stop member 30 prevent telescopic sliding of the connector valve 10 including the valve member 40, from the first tapered recess 21A towards the second tapered recess 21B of the coupler 20. Using the disconnect handle 32, the stop member 30 can be removed allowing the connecting mechanism 28 of the connector valve 10 to be moved from the first tapered recess 21A toward the second tapered recess 21B. By pushing the connector valve 10 a length through the coupler 20, the connector apparatus 50 is actuated into an open configuration as best depicted in FIG. 6. Preferably, the sealing end 42 of the valve member 40 moves from an upstream position relative to the outlet 22 past the region where the outlet 22 is disposed, and moves downstream toward the second outlet 24, thereby opening a flow passage from the end 12 through the outlet 22.

As depicted in FIG. 6, the connector apparatus 50 is shown in an open configuration, where the stop member 30 has been removed. In addition, the connecting mechanism 28 of the connector valve 10 has been moved from the first tapered recess 21A and engaged at the second tapered recess 21B in the same connection manner as the connector valve 10 and first tapered recess 21A described above before moving the connector valve 10 towards the second tapered recess 21B. The locking member 15 with its tapered side 13 only allows movement of the connector valve 10 toward the second retaining recess 21B when the stop member 30 has been removed. This slide connection to the second tapered recess 21B resembles a one-way lock engagement and prevents disconnection between the connector valve 10 and the coupler 20. Preferably, the connecting mechanism 28 allows for a single actuation into the open configuration where the connector apparatus 50 is disposable after one time use.

Preferably, the connector valve 10, permanently engaged to the coupler 20, cannot move back towards the first retaining recess 21A, as the locking member 15 engages the second retaining recess 21B to lock the connector valve 10 in place. The apparatus 50 is actuated to an open configuration. The connection created by the tapered recess 21B and tapered side 13 does not allow for disconnection. The apparatus 50 will remain in an open configuration until it is no longer needed to transport media to a piece of bioprocessing equipment, and can be discarded after one-time use. As shown in FIGS. 5 and 6, the connector valve 10 is illustrated with the hose portion 10b, and the adapter 10a the connecting mechanism 28 are integrally formed together, while the valve member 40 is attached as a separate part. It will be appreciated that alternative configurations may be employed, for instance, the hose, adapter connecting mechanism, and valve member may be attached a separate parts.

Figure 10:
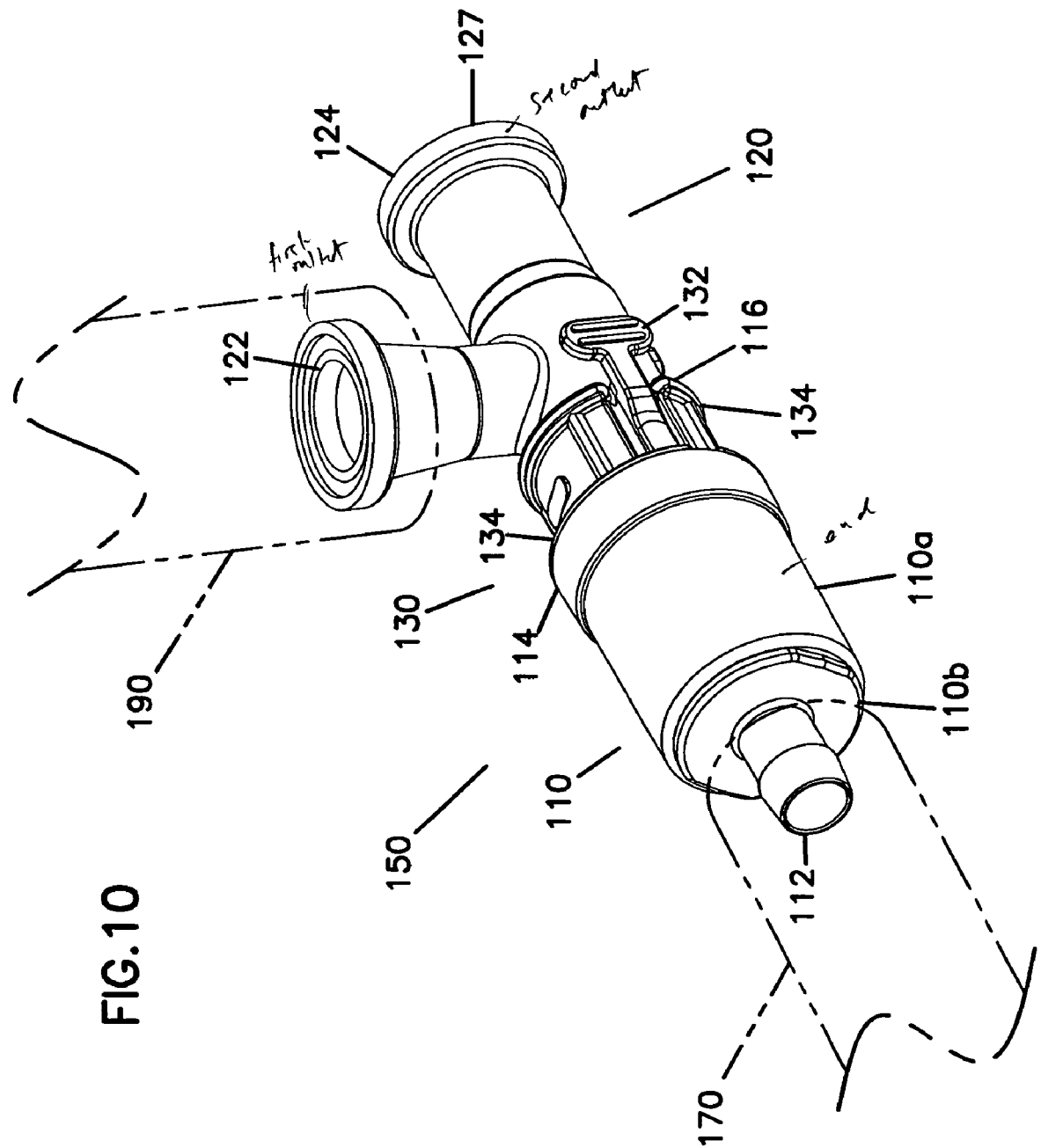
FIG. 10 represents a perspective view another embodiment for a connector apparatus in accordance with the principles of the present invention.
Figure 12:
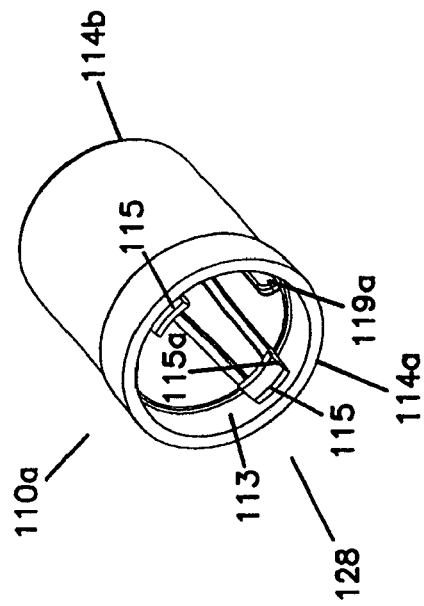
FIG. 12 represents a perspective view of one embodiment of an adapter at a first end for a connector valve as in FIG. 10, in accordance with the principles of the present invention.

FIGS. 10-15 illustrate another preferred embodiment for a connector apparatus 150. The connector apparatus 150 includes a coupler 120, a connector valve 110 that contains an adapter 110a and an end 112 with a valve member 140 connected thereto (shown in FIGS. 13-15). As shown in FIG. 10, the end 112 of the connector valve 110 may include a hose portion 110b suitable for attachment to a media source 170. The adapter 110a includes a connecting mechanism 128 (best shown in FIGS. 14, 15) for connection to the coupler 120. The connecting mechanism 128 includes a locking member 115 and a space 113. As shown in FIGS. 12 and 14-15, the connecting mechanism 128 is formed as a part of the adapter 110a of the connector valve 110. The function of the adapter 110a including the connecting mechanism 128 will be further detailed below. The end 112, as depicted in FIG. 10, is shown as a barbed end for attachment to a media source, such as 170. However, there may be other interfaces that can be used to achieve the same result. Differently from FIGS. 1-8, where the adapter 10a and the end 12 are integrally formed as a one piece structure, FIGS. 10-15 illustrates the adapter 110a and the end 112 as separate parts.

Figure 11:
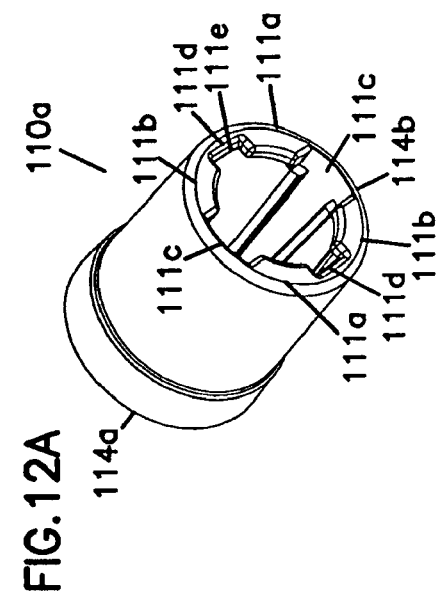
FIG. 11 represents a perspective view of another embodiment of a coupler for a connector apparatus as in FIG. 10, in accordance with the principles of the present invention.

As illustrated in FIGS. 10 and 11, the coupler 120 has an outlet 122 for passage of media and connection to the piece of bioprocessing equipment 190, such as but not limited to a bioreactor. The outlet 122, as depicted in FIG. 10, is shown as a sanitary flange. However, there may be other interfaces that can be used to achieve the same result. Also depicted is a second outlet 124 for allowing steam passage to a steam trap or a condensate outlet. A similar sanitary flange 127, as in the outlet 122, may be disposed at the second outlet 124. However, it will be appreciated that an O-ring seal also can be used at the second outlet 124. In one embodiment, the connector valve 110 and the coupler 120 are telescopically connected, wherein the end 114a of the adapter 110a receives the end 126 and the end 126 receives the sealing end 142 of the valve member 140 of the hose 110b.

The coupler 120 may be insertable through a stop member 130, such that the stop member 130 may be releasably attached around the coupler 120. Stop tabs 134 of the stop member 130 prevent further movement of the connector valve 110 towards the first and second outlets 122 and 124, respectively. One of the stop tabs 134 of the stop member 30 abuts the end 114a of the adapter 110a to restrict telescopic movement between the connector valve 110 and the coupler 120. Another stop tab 134 abuts a seating portion 116 to further restrict movement of the stop member 130 and connector valve 110. Further, the stop member 130 maintains the apparatus 150 in a closed configuration. The stop member 130 further includes a disconnect handle 132, such that removal of the handle 132 allows removal of the entire stop member 130, and the connector apparatus 150 may be actuated to an open configuration. Preferably, the handle 132 is a tear away handle such that tearing the handle 132 enables the entire stop member 130 to be removed. Preferably, the seating portion 116 resides about the outer surface of the coupler 120 and includes at least one space 116a to allow the handle 132 to reside about the outer surface of the coupler 120.

Preferably, in FIG. 11 the coupler 120 includes at least one groove 19 extending along the outer surface of the coupler 120 from the end 126 toward the seating portion 116. Preferably, the coupler includes oppositely disposed grooves 19 as shown in FIG. 11. The function of the groove 119 will be discussed below.

Figure 12A:
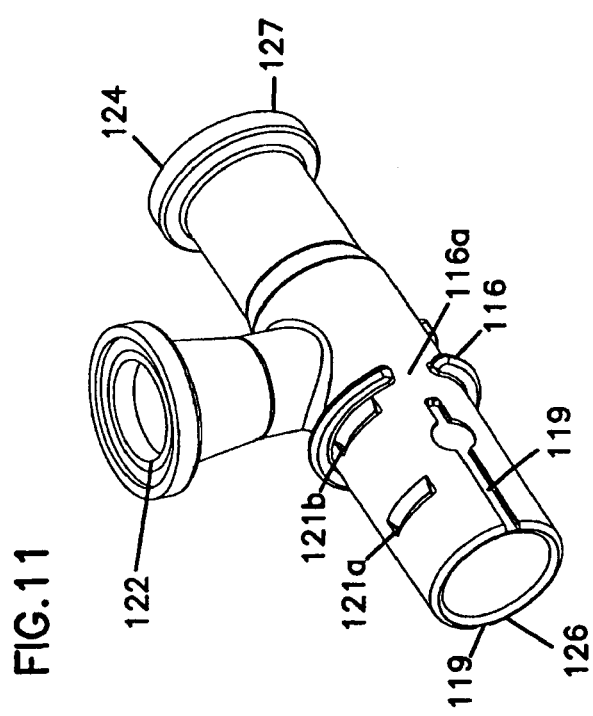
FIG. 12a represents a perspective view of the adapter of FIG. 12 at a second end.

FIGS. 12 and 12a illustrate one preferred embodiment of the adapter 110a for a connector valve 110 that includes a first end 114a and a second end 114b. The connecting mechanism 128 resides at a head portion of the first end 114a, and includes at least one locking member 115 having a space 113. As shown in FIG. 12, two locking members 115 are oppositely disposed on the inner surface of the first end 114a of the adapter 110a. Preferably, the locking members 115 include a tapered side 115a defining a transverse edge for locking with retaining recesses, such as 121A, 121B (discussed below).

A rib 119a extends from the first end 114a toward the second end 114b. Preferably, the rib 119a cooperates with the groove 119 described above in the coupler 120 of FIG. 11, resembling a tongue and groove connection. As shown in FIGS. 11 and 12, one groove 119 and one rib 119a are illustrated. It will be appreciated that oppositely disposed grooves 119 on the coupler 120 and corresponding ribs 119a on the connector valve can be employed, in addition to other configurations. The connection between the groove 119 and rib 119a help hold the connector valve in position and prevent the connector valve 110 from rotating about the outer surface of the coupler, such as coupler 120.

In FIG. 12a, the second end 114b of the adapter 110a includes oppositely disposed first protrusions 111a and second protrusions 111b about the inner surface of the adapter 110a and extend radially inward. Preferably, the first protrusions 111a have a greater width than the second protrusions 111b. Preferably, the oppositely disposed first protrusions 111a are orthogonal to the oppositely disposed second protrusions 111b, and define first gaps 111c and second gaps 111d therebetween. Preferably, at least one of the first and second gaps 111c, 111d are arranged and configured to attach to the hose 110b. As shown in FIG. 12a, the second gaps 111d have a projected surface 111e so as to connect to, for instance, barbed retainers of a hose portion 110b (discussed below). It will be appreciated that the first gaps 111c also may employ a projected surface, such as 111e.

Figure 13:
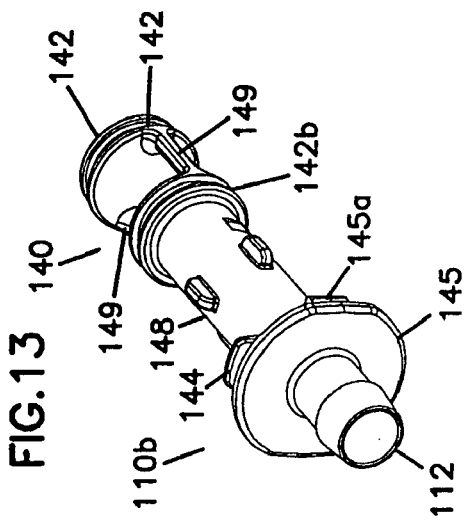
FIG. 13 represents a perspective view of one embodiment of a valve member for a connector valve as in FIG. 10, in accordance with the principles of the present invention.

FIGS. 13-13a illustrate one preferred embodiment of the valve member 140 of the connector valve 110. The valve member 140 includes an elongated body 148 defining a first end 112 and a second end being a sealing end 142. Preferably, the first end is a barbed end and may include a hose portion 110b for suitable attachment to a media source, such as 170. A flange 145 is disposed proximate the first end 112 and includes at least one retention member 145a. Preferably, the retention member 145a is a barbed retainer. Projections 144 extend radially outward from the outer surface of the elongated body 148. As shown in FIG. 13, one retention member 145a and one projection 144 are illustrated. It will be appreciated that a plurality of retention members and projections may be employed. Preferably, inner surface of the first end 112 of the hose 110b includes two oppositely disposed retention members 145a orthogonal to two oppositely disposed projections 144. Preferably, the retention members 145a cooperate with the projected surface 111e of the second gaps 111d in the adapter 110a to engage the hose 110b to the adapter 110a. Additionally, the projections 144 fit through the first gaps 111c to connect the hose 110b and the adapter 110a together.

In FIG. 13a, the sealing end 142 is connected to the elongated body 148 through supports 149 extending longitudinally outward from a sidewall 148a of the elongated body 148. Preferably, two supports 149 are oppositely disposed to connect the sealing end 142 to the elongated body 148. A flow path 146 is defined by the opening at the first end 112 that extends through the elongated body 148.

FIGS. 14 and 15 illustrate an embodiment for the connector apparatus 150 in an initial closed configuration and an embodiment of an open configuration. The coupler 120 and the connector valve 110 operate in a manner similar to the coupler 20 and connector valve 10 described above. In FIG. 14, the coupler 120 is provided with first and second tapered retaining recesses 121A and 121B, respectively, wherein the connector valve 110 is initially disposed at the first retaining recess 121A.

The connector valve 110 further contains the connecting mechanism 128 that includes the at least one locking member 115 and the space 113. As illustrated in FIGS. 12 and 14-15, the connecting mechanism 128 is disposed at the first end 114a of the adapter 110. The locking member 115 of the connecting mechanism 128 engages the first recess 121A of the coupler 120 in the closed configuration, connecting the connector valve 110 to the coupler 120. Preferably the locking member 115 contains a tapered side 115a. The first tapered recess 121A and the tapered side 115a have a connection wherein the first tapered recess 121A has a transverse edge with respect to a tapered portion of the recess 121A that connects with the transverse edge of the locking member 115.

The first tapered recess 121A locks the locking member 115 from moving in a backward direction, and prevents the connector valve 110 from disconnecting from the coupler 120 once they are connected. The tapered portion of the first recess 121A and the tapered side 115a of the locking member 115 allow for forward movement towards the second tapered recess 121B. Preferably, the locking member 115 is a resilient material that is flexible so as to allow the locking member 115 to bend into the space 113 when the connector valve 110 is between engagement with the tapered recesses 121A, 121B, as the connector valve 110 is pushed.

As depicted in FIG. 15, the connector apparatus 150 is shown in an open configuration, where the stop member 130 has been removed. In the open configuration, the sealing end moves past the opening defined by the outlet 122, where the flow path 146 is in fluid communication with the outlet 122 enabling fluid flow. In addition, the connector valve 110 has been moved from the first tapered recess 121A and engaged at the second tapered recess 121B. It will be appreciated that the connection of the connector valve 110 and the second tapered recess 121B is identical as the connector valve 110 and first tapered recess 121A described above before moving the connector valve 110 towards the second tapered recess 121B.

The locking member 115 of the connecting mechanism 128, with its tapered side 115a, allows the connector valve 110 to slide towards the second retaining recess 121B after the stop member 130 has been removed. This slide connection to the second tapered recess 121B resembles a one-way lock engagement and prevents disconnection between the connector valve 110 and the coupler 120. Preferably, the connector valve 110, permanently engaged to the coupler 120, cannot move back towards the first retaining recess 121A, as the locking member 115 engages the second retaining recess 121B to lock the connector valve 110 in place. The apparatus 150 is actuated to an open configuration. The connection created by the tapered recess 121B and tapered side 115a of the locking member 115 does not allow for disconnection. The apparatus 150 will remain in an open configuration until it is no longer needed to transport media to a piece of bioprocessing equipment, and can be discarded after one-time use.

The present invention provides a bioprocessing assembly.

A sterilized connector apparatus, as described above, is included for coupling of a piece of bioprocessing equipment to a media source. The connector apparatus can withstand steam and autoclave conditions. In addition, the connector apparatus can be made of a material such as polycarbonate, or a polysulphone, or a polyphenylsulfide and including other high temperature thermoplastics or materials, which can be injection molded. The media source can be a media bag or other like media vessel. The piece of bioprocessing equipment may be a bioreactor and can include a steam source for sterilization. The dimensions for a bioreactor and media source are specific to the needs of the biomaterial being processed and are further not described here.

FIG. 9 illustrates a flow diagram of a method for coupling a bioreactor with a media source. The method 100 includes providing a connector apparatus, a media source and a piece of bioprocessing equipment 101 as detailed in the above descriptions. The connector apparatus may be as described in the above embodiments, and may be connected to a filled media source 103. The media source and the connector apparatus may be sterilized 105. The media source and a first portion of the connector apparatus can be gamma sterilized. The portion of the connector apparatus being sterilized may include a connector valve and valve member through a portion of a coupler. It will be appreciated that the entire connector apparatus may be gamma sterilized during the first sterilization. A stop member may be connected around the coupler to maintain the connector apparatus in a closed configuration.

The connector apparatus and media source, while maintaining sterilization defined through the media source and the first portion of the connector apparatus can be connected to a piece of bioprocessing equipment 107 in a closed configuration. The piece of bioprocessing equipment may be a bioreactor, which may be sterilized 109 including sterilization of the bioprocessing equipment and a second portion of the coupler. It will be appreciated that the second portion being sterilized may at least partially overlap the sterilized first portion above. After the second sterilization 109, the entire connector apparatus is sterilized. Preferably, after the second sterilization 109 the entire assembly including the media source, connector apparatus, and piece of bioprocessing equipment will be sterilized and ready for use. The second portion of the coupler may be defined by an outlet into the piece of bioprocessing equipment, and through towards a second outlet including a portion of the connecting valve such as sealing head. Preferably, the second outlet is a steam trap or condensate outlet. Preferably, the sterilization 109 of the bioprocessing equipment and the second portion of the coupler are achieved by steam sterilization.

For example, upon connection to the piece of bioprocessing equipment 190, the stop member 130 is removed to allow the connection apparatus 150 to be actuated in an open configuration. By sliding and/or pushing the connector valve 110, which moves telescopically relative to the coupler 120, the connector apparatus 150 can be actuated from an initial closed configuration to an open configuration. Pushing the valve member 140 a length through the coupler 120 opens a flow passage defined between the end 112 of the connector valve and the outlet 122 of the coupler 120, thereby allowing media flow from the media source 170 to the piece of bioprocessing equipment 190.

The pulling, sliding or pushing of the connector valve 110 resembles a one-way lock engagement and prevents disconnection between the connector valve 110 and the coupler 120. When media flow to the piece of bioprocessing equipment 190 is no longer needed the connector apparatus 150 and media source 170 can be discarded after one time use.

As stated above, the connector apparatus provides a more convenient and practical way of connecting bioprocessing equipment with a media source. Further, being disposable and intended for one-time use, the connector apparatus allows for the elimination of laminar flow hoods and multiple valves and steam traps that are used in sterilization. In addition, the connector apparatus provides a versatile means for coupling that can be easily modified to accommodate a range of needs with respect to particular biomaterials processed.

Having described the embodiments of the present invention, modifications and equivalents may occur to one skilled in the art. It is intended that such modifications and equivalents shall be included with the scope of the invention.

We claim:

1. A method for connecting an assembly for bioprocessing comprising:

providing a filled media source connected to a connector apparatus, and a piece of bioprocessing equipment, the connector apparatus including a connector valve, a coupler, a valve member, and a stop member;

subjecting the filled media source and at least a first portion of the connector apparatus to a first sterilization;

coupling the filled media source to the piece of bioprocessing equipment using the connector apparatus;

subjecting the piece of processing equipment and a second portion partially overlapping the first portion of the connector apparatus to a second sterilization, thereby sterilizing the connector apparatus in a connected state;

actuating the connector apparatus to enable media flow through the connector apparatus to the piece of bioprocessing equipment.

2. The method for connecting an assembly for bioprocessing according to claim 1, wherein the step subjecting the filled media source and a portion of the connector apparatus to a first sterilization includes maintaining the first sterilization before and during connection with the bioprocessing equipment.

3. The method for connecting an assembly for bioprocessing according to claim 1, wherein actuating the connector apparatus includes pushing the valve member through the coupler from a closed configuration to an open configuration.

4. The method for connecting an assembly for bioprocessing according to claim 1, wherein the step of subjecting to a first sterilization includes sterilizing the entire connector apparatus.

5. The method for connecting an assembly for bioprocessing according to claim 1, wherein the step of subjecting to a second sterilization includes sterilizing the entire assembly for bioprocessing.

6. The method for connecting an assembly for bioprocessing according to claim 1, wherein providing the filled media source connected to the connector apparatus further comprises providing the coupler including an end and first and second outlets, and the connector valve being connectable at a first end to the filled media source, the connector valve comprising an adapter and the valve member, the adapter containing a connecting mechanism being engageable with the end of the coupler, the valve member being partially disposed within the adapter and insertable into the coupler, wherein the connector apparatus defines a flow passage being actuatable from a closed configuration to an open configuration when the coupler and the connector valve are engaged, wherein the valve member forms a fluid tight seal upstream of the first outlet of the coupler in the closed configuration, wherein the valve member forms a fluid tight seal downstream of the first outlet of the coupler in the open configuration, and wherein the second outlet is in fluid communication with the first outlet when the coupler is in the closed configuration.

* * * * *